(12) United States Patent
Diaz et al.

(10) Patent No.: US 6,540,768 B1
(45) Date of Patent: Apr. 1, 2003

(54) VASCULAR FILTER SYSTEM

(75) Inventors: Pedro L. Diaz, Pembroke Pines, FL (US); Mark L. Pomeranz, Weston, FL (US); Robert Letendre, Miami, FL (US); Mark Inderbitzen, Miramar, FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/501,543

(22) Filed: Feb. 9, 2000

(51) Int. Cl.[7] .................................................. A61M 29/00
(52) U.S. Cl. ...................................................... 606/200
(58) Field of Search ................................ 606/200, 159, 606/108, 127, 114, 113

(56) References Cited

U.S. PATENT DOCUMENTS

| | | | |
|---|---|---|---|
| 3,952,747 A | 4/1976 | Kimmell, Jr. ............ 128/303 R |
| 4,425,908 A | 1/1984 | Simon ......................... 128/1 R |
| 4,688,553 A | 8/1987 | Metals ........................ 128/1 R |
| 4,723,549 A | 2/1988 | Wholey et al. ............. 128/344 |
| 4,727,873 A | 3/1988 | Modin-Uddin .......... 128/303 R |
| 4,790,812 A | 12/1988 | Hawkins, Jr. et al. ........ 604/22 |
| 4,794,928 A | 1/1989 | Kletschka .................... 128/344 |
| 4,842,579 A | 6/1989 | Shiber ........................... 604/22 |
| 4,873,978 A | 10/1989 | Ginsburg .................... 128/345 |
| 4,921,484 A | 5/1990 | Hillstead .................... 604/104 |
| 4,926,858 A | 5/1990 | Gifford, III et al. ........ 606/159 |
| 4,969,891 A | 11/1990 | Gewertz ..................... 606/200 |
| 5,053,008 A | 10/1991 | Bajaj ........................... 604/104 |
| 5,092,839 A | 3/1992 | Kipperman ................... 604/53 |
| 5,108,419 A | 4/1992 | Reger et al. ................ 606/200 |
| 5,152,777 A | 10/1992 | Goldberg et al. ........... 606/200 |
| 5,160,342 A | 11/1992 | Reger et al. ................ 606/200 |
| 5,329,942 A | 7/1994 | Gunther et al. ............. 128/898 |
| 5,376,094 A | 12/1994 | Kline .......................... 606/113 |
| 5,421,832 A | 6/1995 | Lefebvre ....................... 604/53 |
| 5,443,498 A | 8/1995 | Fontaine ......................... 623/1 |
| 5,449,372 A | 9/1995 | Schmaltz et al. ........... 606/198 |
| 5,484,418 A | 1/1996 | Quiachon et al. ........... 604/167 |
| 5,507,767 A | 4/1996 | Maeda et al. ............... 606/198 |
| 5,527,354 A | 6/1996 | Fontaine et al. ................ 623/1 |
| 5,549,626 A | 8/1996 | Miller et al. ................ 606/200 |
| 5,569,274 A | 10/1996 | Rapacki et al. ............. 606/158 |
| 5,569,275 A | 10/1996 | Kotula et al. ............... 606/159 |
| 5,649,953 A | 7/1997 | Lefebvre ..................... 606/200 |
| 5,681,347 A | 10/1997 | Cathcart et al. ............ 606/200 |
| 5,695,519 A | 12/1997 | Summers et al. ........... 606/200 |
| 5,769,816 A | 6/1998 | Barbut et al. ................. 604/96 |
| 5,800,525 A | 9/1998 | Bachinski et al. .............. 623/1 |
| 5,814,064 A | 9/1998 | Daniel et al. ............... 606/200 |
| 5,827,324 A | 10/1998 | Cassell et al. .............. 606/200 |
| 5,908,435 A | 6/1999 | Samuels ...................... 606/200 |
| 5,925,062 A | 7/1999 | Purdy ......................... 606/200 |

FOREIGN PATENT DOCUMENTS

| | | | | |
|---|---|---|---|---|
| EP | 0 553 511 A1 | 3/1993 | .......... | A61M/29/02 |
| EP | 0 686 379 A3 | 12/1995 | ............ | A61F/2/06 |
| EP | 0 686 379 A2 | 12/1995 | ............ | A61F/2/06 |
| EP | 0 696 447 A2 | 2/1996 | ............ | A61F/2/06 |
| EP | 0 696 447 A3 | 2/1996 | ............ | A61F/2/06 |
| WO | WO 96/01591 | 1/1996 | .......... | A61B/17/22 |
| WO | WO 96/23441 | 8/1996 | ............ | A61B/5/00 |
| WO | WO 98/33443 | 8/1998 | .......... | A61B/17/22 |
| WO | WO 99/22673 | 5/1999 | ............ | A61F/2/01 |
| WO | WO 99/23976 | 5/1999 | ............ | A61E/2/01 |

*Primary Examiner*—Kevin T. Truong

(57) ABSTRACT

A removable vascular filter system for blocking micro- and macro-emboli while allowing the continued perfusion of blood comprises a filter membrane positioned on a guidewire, wherein a free end of the membrane sits tightly against the guidewire when the filter membrane is in a collapsed state and wherein the filter has a means for deploying the filter membrane to assume a position substantially normal to the longitudinal axis of the guidewire. The filter membrane is comprised of a fine mesh material which has a pore size capable of blocking emboli while allowing continued blood flow, a preferred embodiment of which comprises regularly spaced, laser-formed holes, and in which the membrane has a scalloped proximal profile.

5 Claims, 21 Drawing Sheets

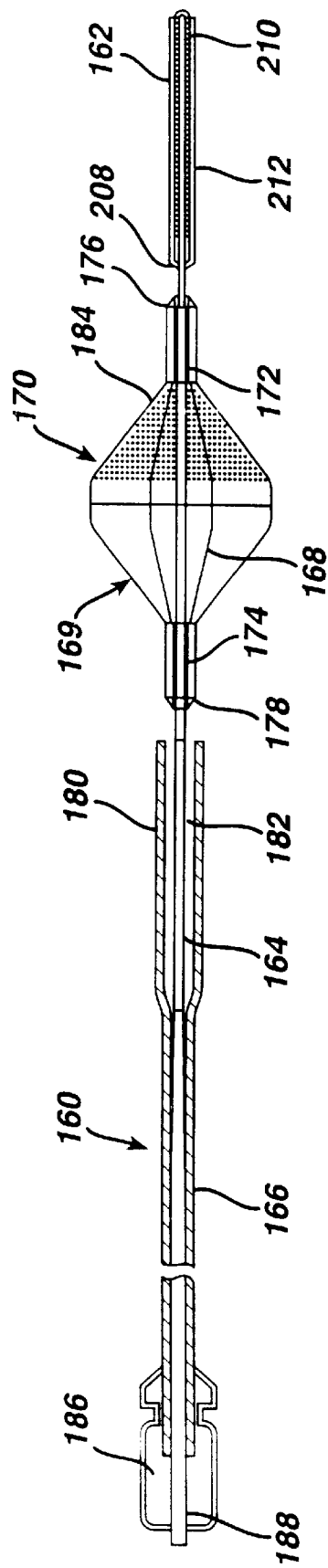
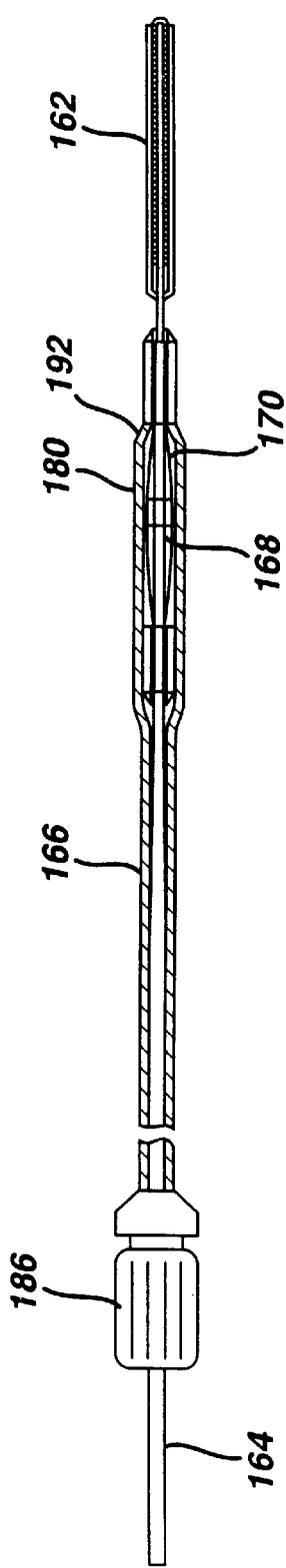

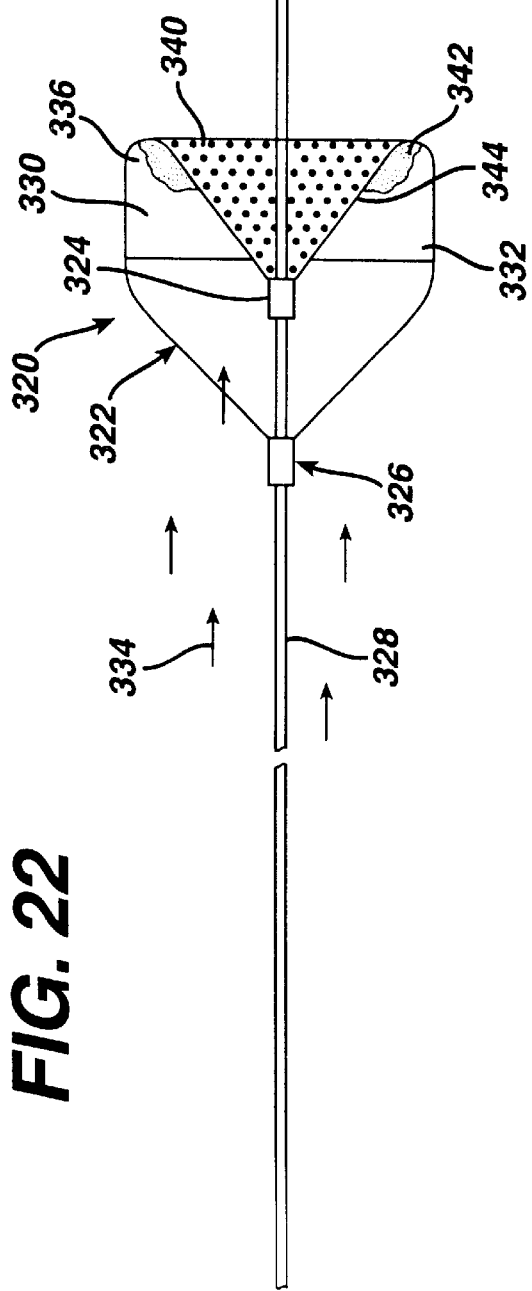
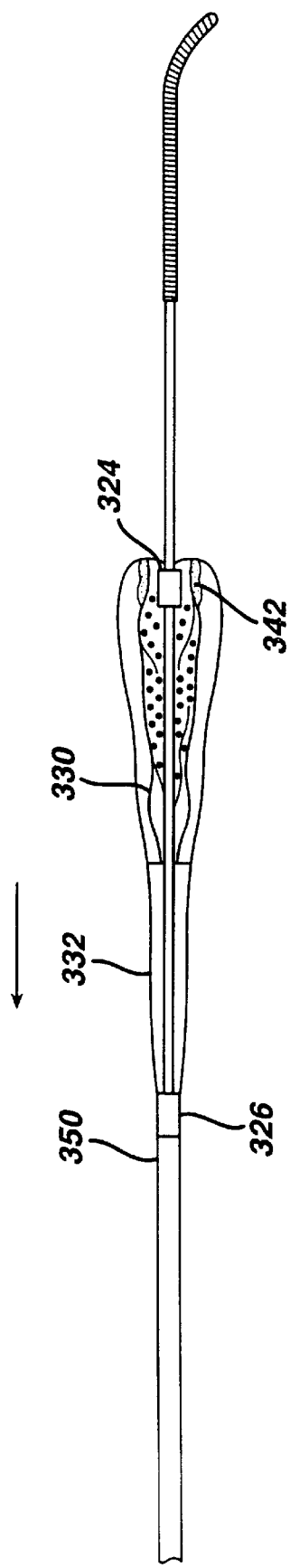

VASCULAR FILTER SYSTEM

FIELD OF THE INVENTION

The present invention relates to the treatment of vascular disease during either surgery or percutaneous angioplasty and stenting. More particularly, the invention relates to a system that reduces macro- and micro-embolization during the treatment of vascular stenosis.

BACKGROUND OF THE INVENTION

A variety of surgical and non-surgical procedures have been developed for removing obstructions from blood vessels. Balloon angioplasty utilizes a balloon-tipped catheter which may be inserted within a stenosed region of the blood vessel. By inflation of the balloon, the stenosed region is dilated. Surgery involves either removing the plaque from the artery or attaching a graft to the artery so as to bypass the obstructing plaque. Other techniques, such as atherectomy, have also been proposed. In atherectomy, a rotating blade is used to shave plaque from an arterial wall.

One problem common with all of these techniques is the accidental release of portions of the plaque or thrombus, resulting in emboli which can lodge elsewhere in the vascular system. Such emboli are extremely dangerous to the patient, frequently causing severe impairment of the distal circulatory bed. Depending upon the vessel being treated, this may result in stroke, myocardial infarction or limb ischemia.

During a postoperative period vascular filters are used, when there is a perceived risk of the patient encountering a pulmonary embolus resulting from the lots generated at the surgical site. As a typical use of vascular filters, the filter is mounted in the vena cava to catch large emboli passing from the surgical site to the lungs.

Permanent implantation of a filter is often medically undesirable, yet it has been done because vascular filters are implanted in patients primarily in response to potentially life threatening situations. Accordingly, permanent implantation of a vascular filter is often accepted.

Nonetheless, avoid permanent implantation, it would be desirable to provide an apparatus and method for preventing embolization associated with conventional surgery and angioplasty procedures. In particular, it would be desirable to provide a device which could be located within the vascular system to collect and retrieve portions of plaque and thrombus which have dislodged during the surgery or angioplasty procedure.

OBJECT OF THE INVENTION

This invention provides a vascular filter system for reducing macro- and micro-embolization.

It also provides a vascular filter system which is readily removable from the vascular system of a patient when the filter is no longer needed.

Further, it provides a vascular filter system having a configuration which does not require hooks to penetrate and grip the blood vessel walls, so that filter deployment results in less blood vessel injury.

Further the invention provides a vascular filter system of very low profile which is delivered along a guidewire and can be used in small vessels.

The invention will become more readily apparent from the description below.

SUMMARY OF THE INVENTION

The present invention generally relates to a vascular filter system useful in the treatment of vascular disease, in particular, a percutaneous angioplasty and stenting system useful, for example, in the treatment of carotid arterial stenoses. Macro- and micro-embolization occurs during such angioplasties, which increases the risk of stroke. The system of the present invention is useful in preventing such risk. This system is also useful in any procedure in which embolization is a risk.

The vascular filter system of the present invention decreases embolic events while allowing distal tissue perfusion. The filter is incorporated into a guidewire which is used during the entire procedure, from first crossing of a lesion through deploying a stent. In one embodiment, the filter consists of a thin membrane attached to the guidewire and supported by fine metal spines. Attachment of filter to guidewire allows membrane expansion, to provide a firm fit inside the artery. Also, the system allows collapse of the filter membrane at the end of the procedure, so that it fits tightly against the guidewire and is withdrawn through the guide catheter.

In another embodiment, the membrane rests upon or is attached to a basket-like structure, at least one end of which is attached to the guidewire. The membrane has a pore size such that blood flow is not impeded when the filter membrane is expanded, but through which micro- and macro-emboli are blocked. Expansion of the filter membrane is aided by the forward flow of blood against the filter. The filter design results in a very low profile so that the initial go crossing of the lesion via the guidewire is minimally traumatic. Also, small diameter and narrow profile facilitate use of the device in smaller or larger arteries with minimal or no obstruction of blood flow.

Further embodiments of this filter membrane and its deployment system are provided without departing from the general nature of the guidewire based system. Among those are various modifications of the folding made to the filter membrane, and its configuration.

BRIEF DESCRIPTION OF THE DRAWINGS

The above advantages of the invention will be apparent upon consideration of the following detailed description, taken in conjunction with the accompanying drawings. In these drawings, reference characters refer to like parts throughout.

FIG. 14 is a lateral, partial cross-sectional view of one embodiment of the invention with the filter membrane in an open position;

FIG. 15 is a lateral, partial cross-sectional view of the embodiment of the invention in FIG. 14 with the sheath closed;

FIG. 22 is a schematic, partial cross-sectional view of another embodiment of the invention where the distal section of the filter basket is inverted;

FIG. 23 is a schematic, partially cross-sectional view of the embodiment shown in FIG. 22 where the filter basket is collapsed.

DETAILED DESCRIPTION OF THE INVENTION

The present invention relates to a vascular filter system for use in percutaneous angioplasty and stenting and provides for the prevention of distal embolism during endovascular procedures. Further, the filter system of the invention allows for distal perfusion while preventing embolization.

The system comprises a thin, perforated filter membrane which is capable of blocking emboli and which is attached to the distal end of a guidewire. In one embodiment the system uses thin fibers which are moveable and are attached to or encapsulated by the filter membrane to deploy and/or collapse the filter membrane. The invention also contemplates the use of metal spines or inflatable spines attached to the filter membrane to deploy the filter membrane. The fibers or spines can also be attached to a moveable core which is slidable within the guidewire and is used to deploy and collapse the filter membrane.

The filter membrane deploys in an umbrella-like fashion with the unattached edge of the membrane moving upward, i.e., distally, and outward until it is in firm contact with an artery wall. When the filter membrane is deployed, it spans the cross-sectional area of the vessel lumen being treated for a stenosis such as carotid stenosis, or another condition likely to produce emboli.

In another, preferred embodiment of the invention, a thin, flexible, perforated membrane is supported by four or more supports that form a distally extending basket. At least one end of the basket is attached to the guidewire, and the other, slidable end can be moved to cause the membrane to open or close.

Figure 1:
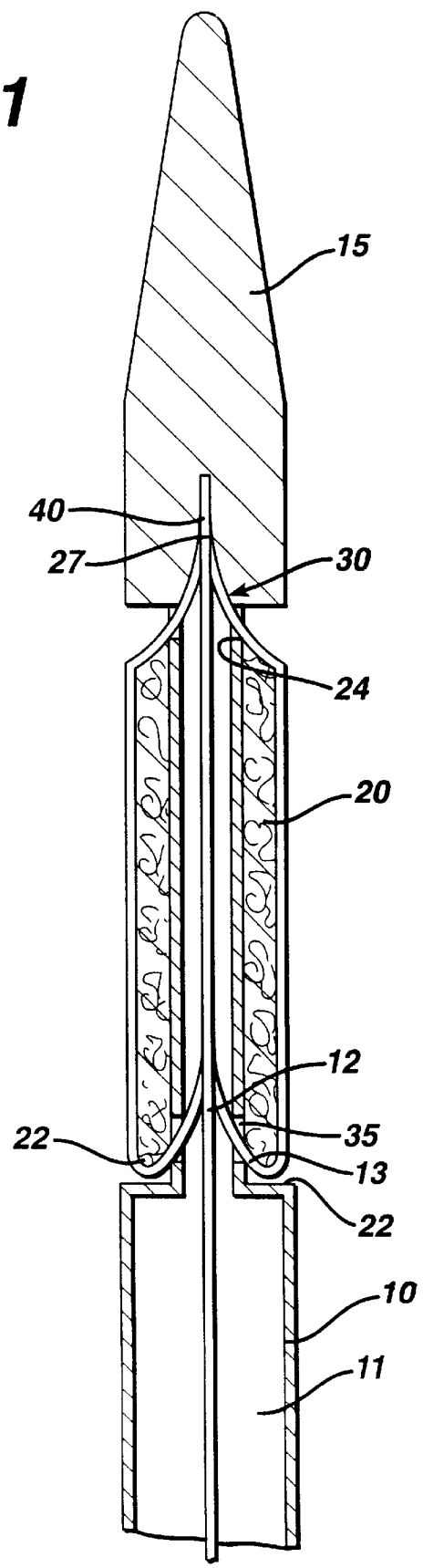
FIG. 1 is a lateral, partial cross-sectional view of the distal end of a guidewire of one embodiment of the invention, with the filter membrane in a collapsed position.

The invention can be appreciated by reference to the drawings. FIG. 1 illustrates a lateral, cross-sectional view of a distal end of a guidewire 10 with a filter membrane 20 attached thereto. FIG. 1 shows guidewire 10 with a shapeable, tapered soft tip 15 at its extreme distal end which provides flexibility and maneuverability to guidewire 10. The filter membrane in FIG. 1 is in a collapsed position. Filter membrane 20 has a fixed portion 24 which is movably attached to guidewire 10, and filter membrane 20 lies adjacent guidewire 10 proximal to fixed portion 24 when filter membrane 20 is in the collapsed state. A moveable core 40 runs through a center lumen 11 of guidewire 10 and preferably extends distally a short distance beyond fixed portion 24 of filter membrane 20. Deploying wires or fibers 30 are each firmly attached at one end 27 to moveable core 40 distal to fixed portion 21 of filter membrane 20. The deploying fibers 30 are attached at their other ends to filter membrane 20 at attachment points 22.

Collapsing fibers 35 are each firmly attached at one end 12 to the portion of moveable core wire 40 which is interior to filter membrane 20 when it is in the collapsed state. Collapsing fibers 35 are each attached at their other end 13 to filter membrane 20 at attachment points 22. Accordingly, collapsing fibers 35 lie interior to filter membrane 20 when filter membrane 20 is in the collapsed state.

Filter membrane 20 is deployed when the operator pulls moveable core 40 proximally through the interior of guidewire 10. Prior to retraction of moveable core 40, deploying fibers 30 are sufficiently relaxed so as not to create any tension at filter membrane attachment points 22. Upon retraction of moveable core 40, tension is created in deploying fibers 30.

There will preferably be from 2 to 6 evenly-spaced deploying fibers 30 and collapsing fibers 35, with 3 or 4 such fibers 30, 35 being most preferred. The deploying fibers 30 and collapsing fibers 35 can be made of any flexible, medically acceptable material, including stainless steel, nitinol, another metal or metallic alloy, a non-metallic substance such as graphite, or a suitable polymer. In addition, guidewire 10 and moveable core 40 can be made from similar materials. Typically, guidewire 10 has an external diameter of from about 0.014 in. to about 0.035 in., a wall thickness between about 0.002 in. to about 0.010 in., and a length between about 25 cm to about 300 cm. Also, moveable core 40 could have a diameter of from about 0.003 in. to about 0.010 in. and a length of from about 30 cm to about 350 cm.

Figure 2:
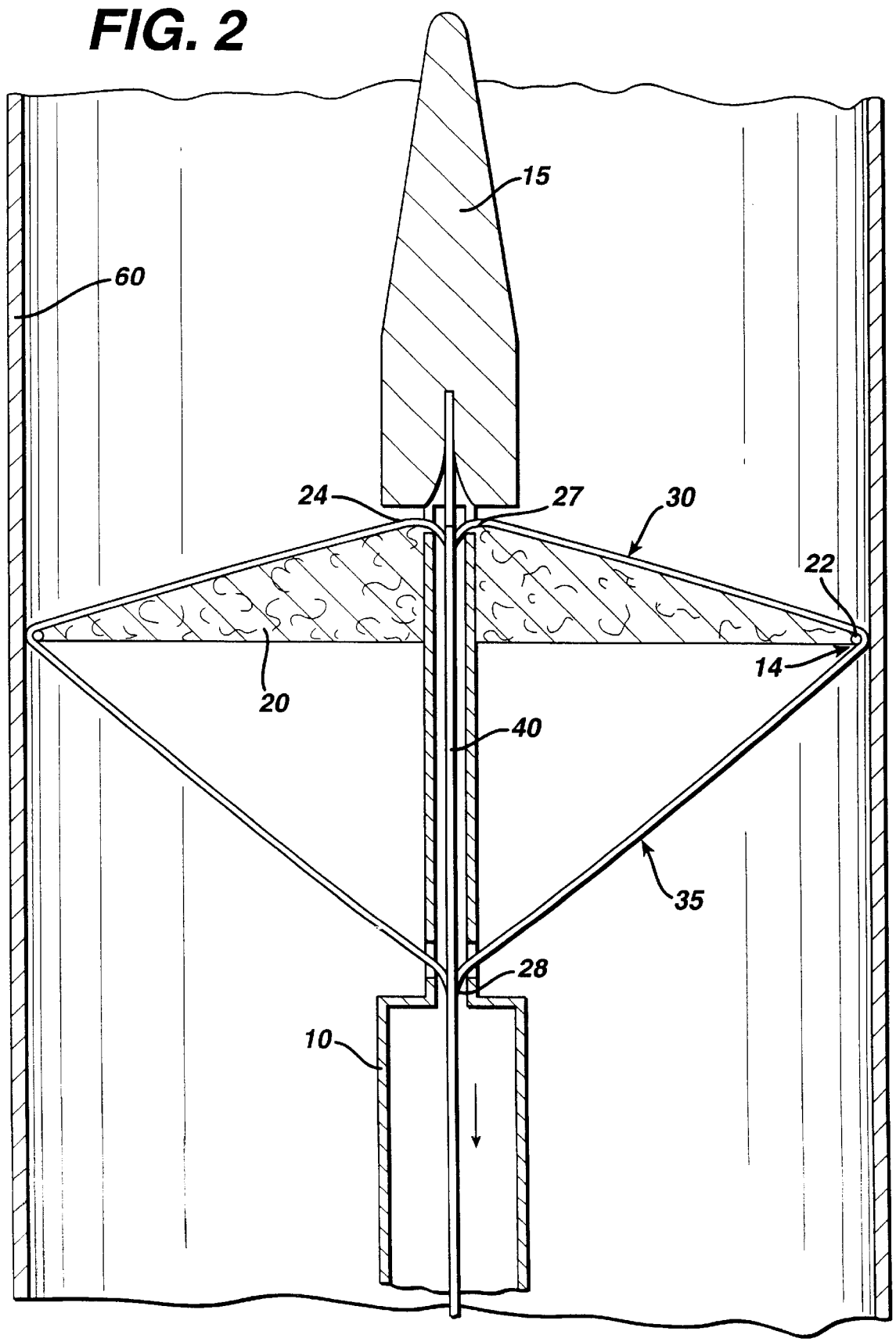
FIG. 2 is a lateral, partial cross-sectional view of the distal end of a guidewire of FIG. 1 with the filter membrane in an expanded, deployed position.

FIG. 2 illustrates the filter device of the invention in a deployed position on the inside of an artery wall 60. Moveable core 40 is in a retracted state, i.e., pulled proximally through the interior of guidewire 10. Tension is created in deploying fibers 30, and filter membrane 20 extends to a deployed position, where the outer edge 14 of filter membrane 20 contacts artery wall 60. In this deployed position, collapsing fibers 35 are in a relaxed state and extend from filter membrane attachment points 22 to fixed attachment points 28 on moveable core 40.

The flow of blood in FIG. 2 is toward the distal end of guidewire 10. As such, the force of the flow of blood pushed on deployed filter membrane 20 and helps to maintain filter membrane 20 in the deployed position.

For withdrawal of guidewire 10 and the filter device, filter membrane 20 is collapsed so that it sits tightly against guidewire 10. This is accomplished by extending moveable core 40 distally through guidewire 10, thus relaxing deploying fibers 30 and creating tension in collapsing fibers 35. The tension in collapsing fibers 35 collapses the filter membrane 20, allowing it to fit tightly against guidewire 10 in the recess 16, as depicted in FIG. 1.

Figure 3:
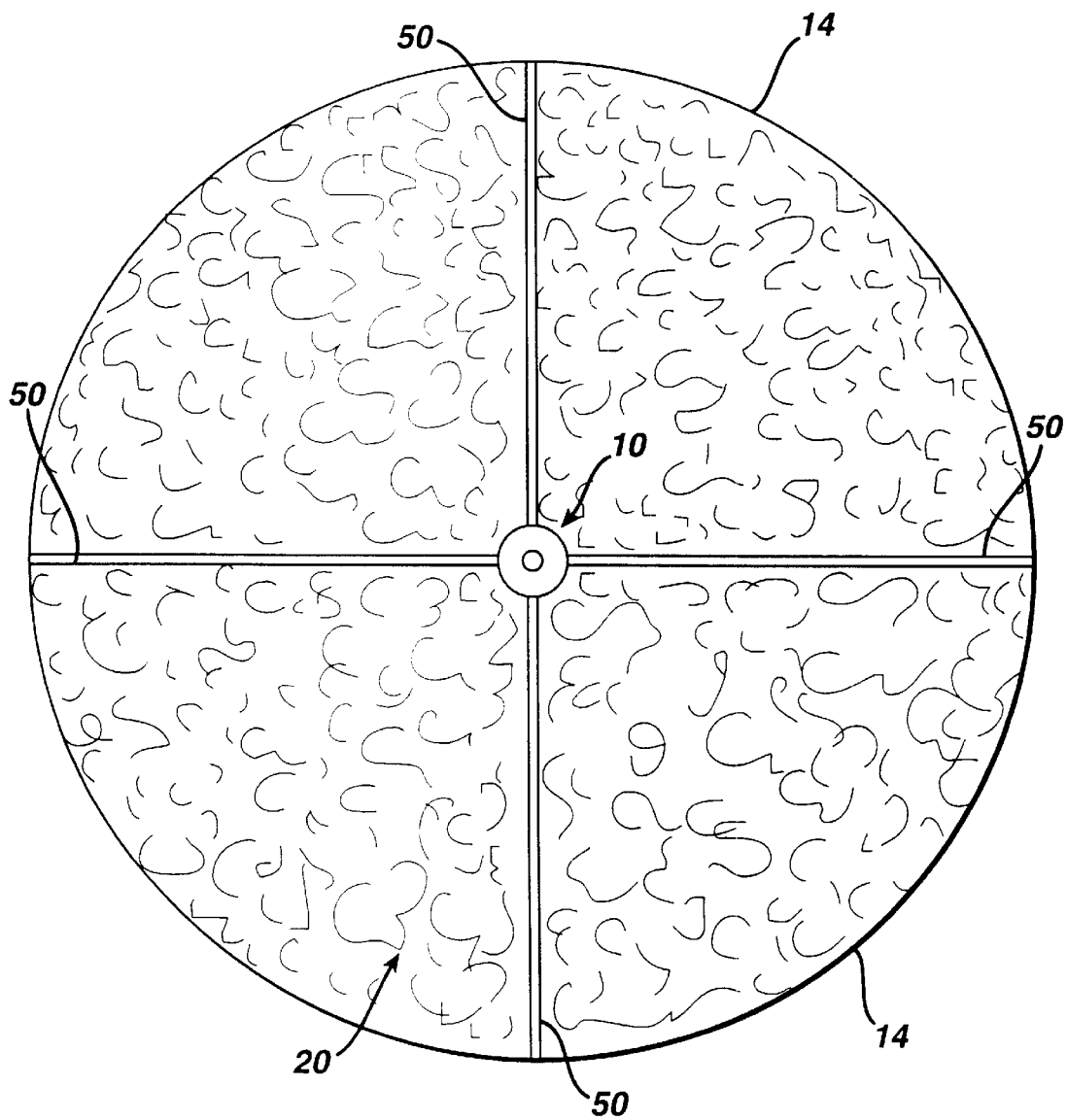
FIG. 3 is a proximal end-on view of the filter membrane shown in FIG. 2.

FIG. 3 illustrates the filter device of the invention from a distal end view in FIG. 2, with filter membrane 20 deployed. Guidewire 10 is centrally located, and structural wires 50 are seen extending from guidewire 10 to the outer edge 14 of filter membrane 20. These wires 50 provide structural integrity and rigidity to filter membrane 20. FIG. 3 depicts four, evenly-spaced structural wires 50, but there can be more or less structural wires 50. Preferably there are from two to six structural wires 50. The wires 50 may preferably be made of stainless steel or another medically acceptable metal or alloy.

Filter membrane 20 of the invention is preferably a mesh such as that depicted in FIG. 3. The mesh should have pores of a size sufficient to block and capture any micro- and macro-emboli which may flow downstream from the site where the stenosis is being treated, but large enough such that blood flow is not impeded. The mesh used in the filter device of the invention can have a pore size less than 300 microns, preferably from about 50 to about 150 microns. Moreover, the distance from guidewire 10 to free ends 22 allows a firm fit between filter membrane 20 and artery wall 60. The diameter of filter membrane 20 will be directly related to the artery being treated, with typical diameters ranging from less than about 2 mm to about 40 mm, most preferably from about 2 mm to about 20 mm.

The membrane can be comprised of fabric or non-fabric meshes, such as those used in known hemodialysis filters or heart-lung bypass machine filters. Suitable materials include polymers or physiologically acceptable metals or alloys.

Figure 4:
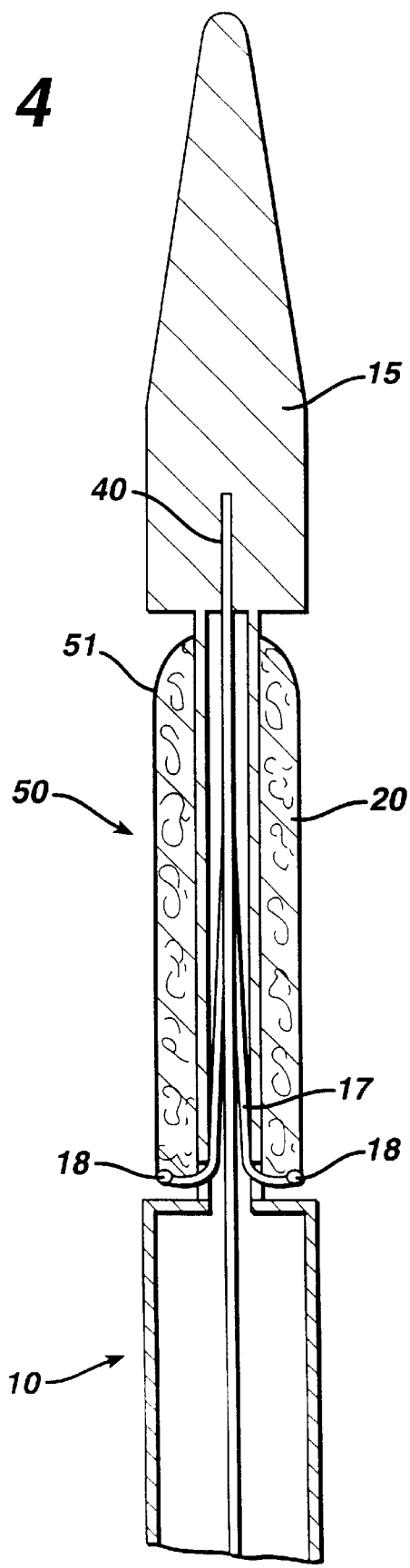
FIG. 4 is a lateral, partial cross-sectional view of another embodiment of the invention.
Figure 5A:
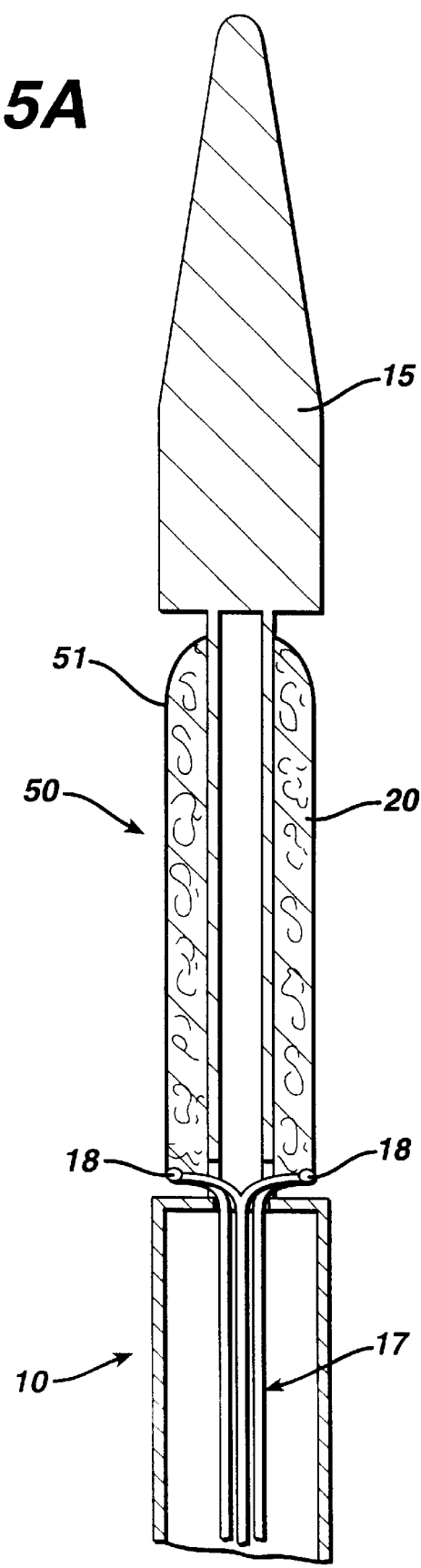
FIG. 5A is a lateral, partial cross-sectional view of a further embodiment of the invention.
Figure 5B:
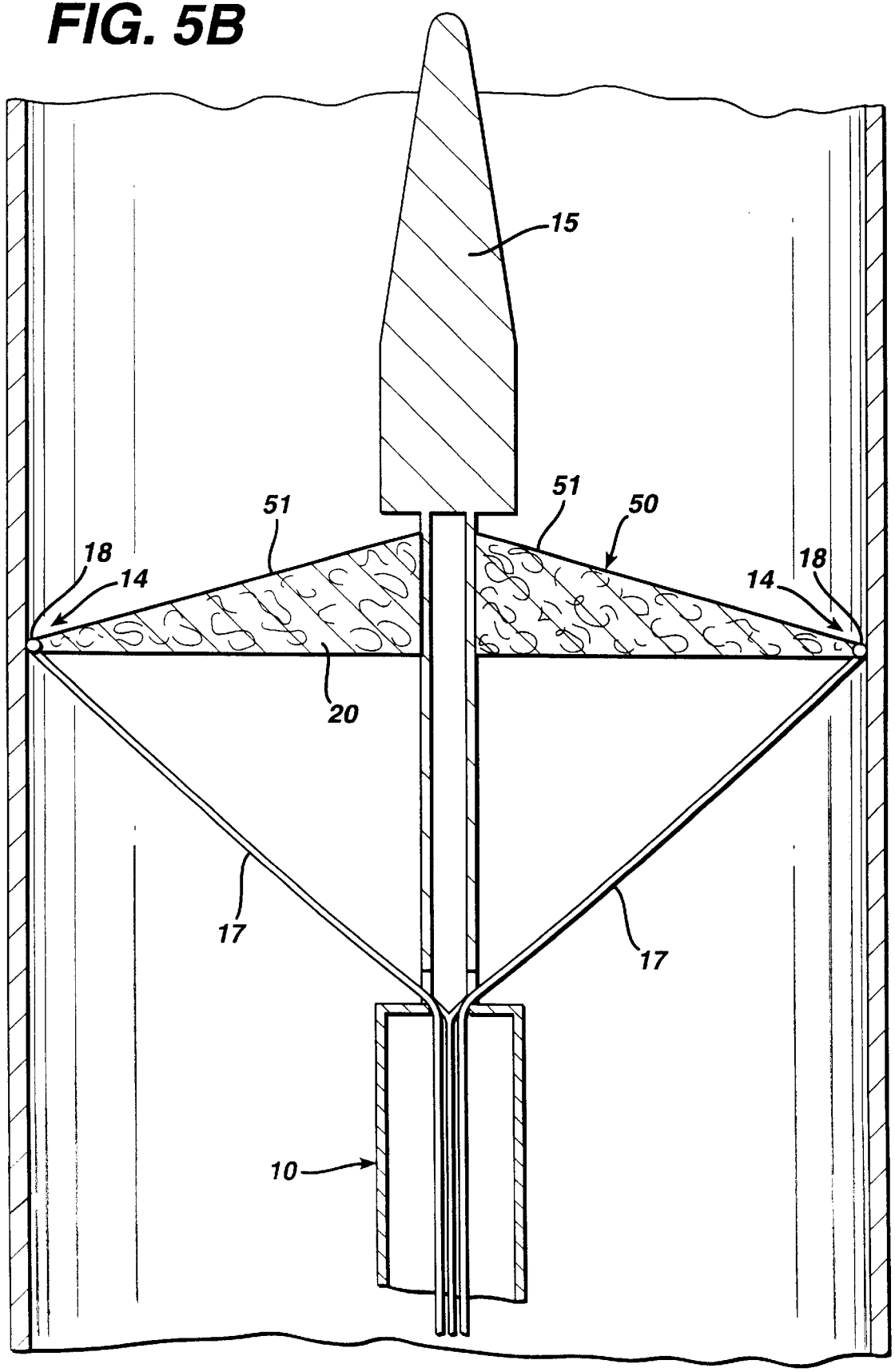
FIG. 5B is a lateral, partial cross-sectional view of the embodiment of the invention shown in FIG. 5A with the filter membrane in an expanded, deployed position.

In alternative embodiments of the invention seen in FIGS. 4, 5A and 5B, filter membrane 20 is suspended between from two to eight, preferably from four to eight, thin metal wires 51 which serve as spines for filter membrane 20. Wires 51 may be comprised of stainless steel or another metallic alloy, nitinol, or another shape-memory material. Wires 51 are constructed so that they assume a 90° angle with guidewire 10 when they are in an unconstrained state. This will result in expansion of the filter membrane 20 to a position normal to guidewire 10. A set of thin fibers 17 are attached at attachment points 18 to filter membrane outer edge 14 and are used to collapse filter membrane 20.

FIG. 4 shows an embodiment of this invention in which metal wires 51 are allowed to regain their unconstrained 90° angle state by use of a moveable core 40 that runs through guidewire 10. Prior to retraction of moveable core 40, fibers 17b are sufficiently tensed so as to restrain wires 51. Upon retraction of moveable core 40, tension in fibers 17 is released and wires 51 are allowed to revert to their relaxed shape, which will result in expansion of filter membrane 20 to a position normal to guidewire 10.

FIGS. 5A and 5B show an embodiment of the invention wherein wires 51 are restrained by fibers 17 that run through guidewire 10 and that are controlled at a remote location. In FIG. 5A, there is sufficient tension in fibers 17 to maintain wires 51 in a constrained position. In FIG. 5B, tension in fibers 17 has been relaxed such that wires 51 are allowed to revert to their relaxed shape, which will result in expansion of filter membrane 20 to a position normal to guidewire 10.

Figure 6:
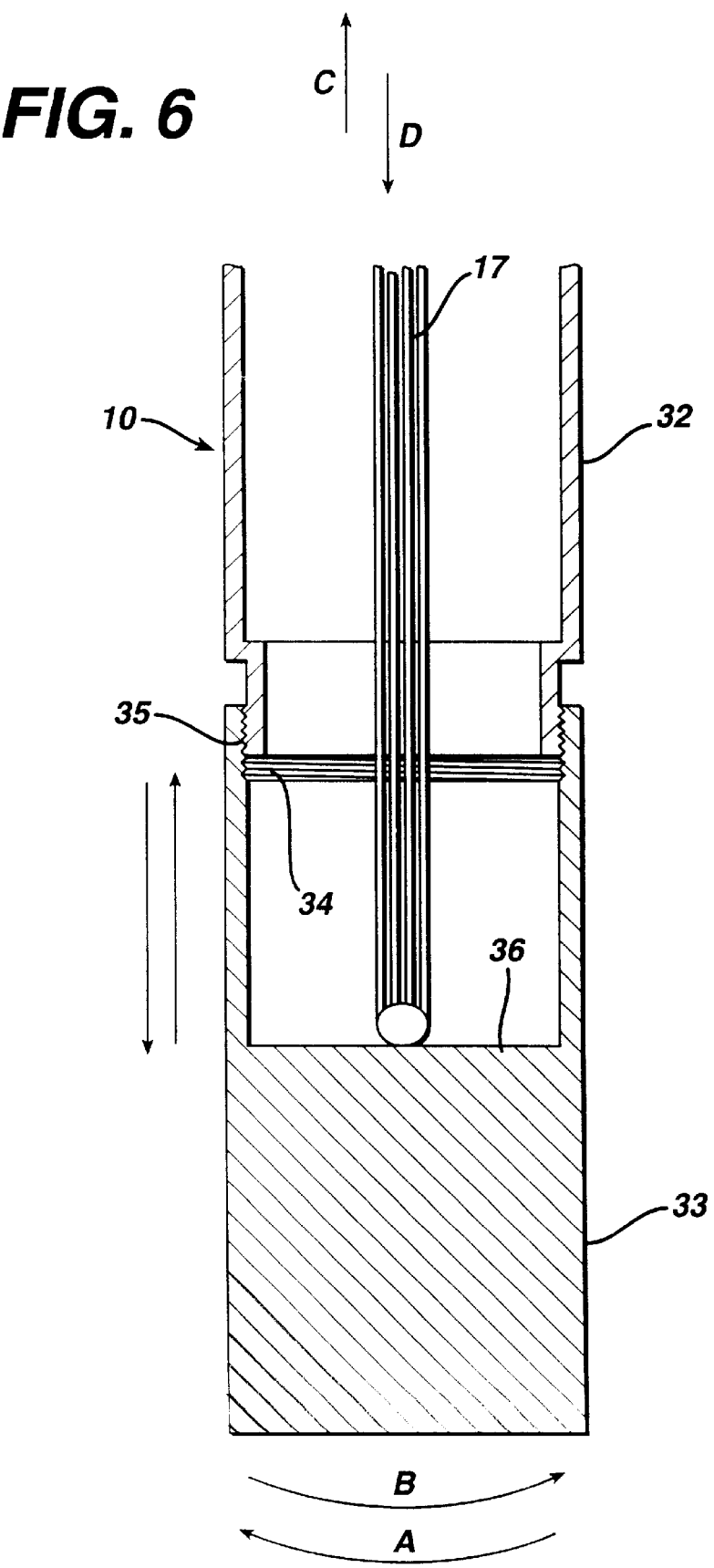
FIG. 6 is a partial cross-sectional view of a control handle for the invention.

FIG. 6 depicts a control handle especially suitable for the embodiment of the invention shown in FIGS. 5A and 5B. The proximal end 32 of guidewire 10 is rotatably attached to handle 33, such that rotation causes handle 33 to move relative to proximal guidewire end 32. For example, handle 33 may have threads 34 which engage threads 35 on guidewire proximal end 32. Fibers 17 attached to filter membrane 20 are secured in a base 36 of handle 33. Then, as handle 33 is turned, the fibers 17 move distally or proximally to open or close filter membrane 20.

As handle 31 is turned clockwise in the direction of arrow A and fibers 17 are allowed to move distally in the direction of arrow C, the tension on the filter membrane fibers 17 decreases, and wires 51 are allowed to assume their natural 90° angle with respect to the guidewire, resulting in opening of filter membrane 20. Similarly, when handle 33 is turned counterclockwise is the direction of arrow D, the tension on filter fibers 17 increases, causing filter membrane 20 to collapse tightly against guidewire 10. Of course, the direction of turn of handle 33 as discussed above can be reversed, as long as threads 34, 35 are properly formed to allow appropriate movement of handle 33 relative to guidewire proximal end 32.

Figure 11:
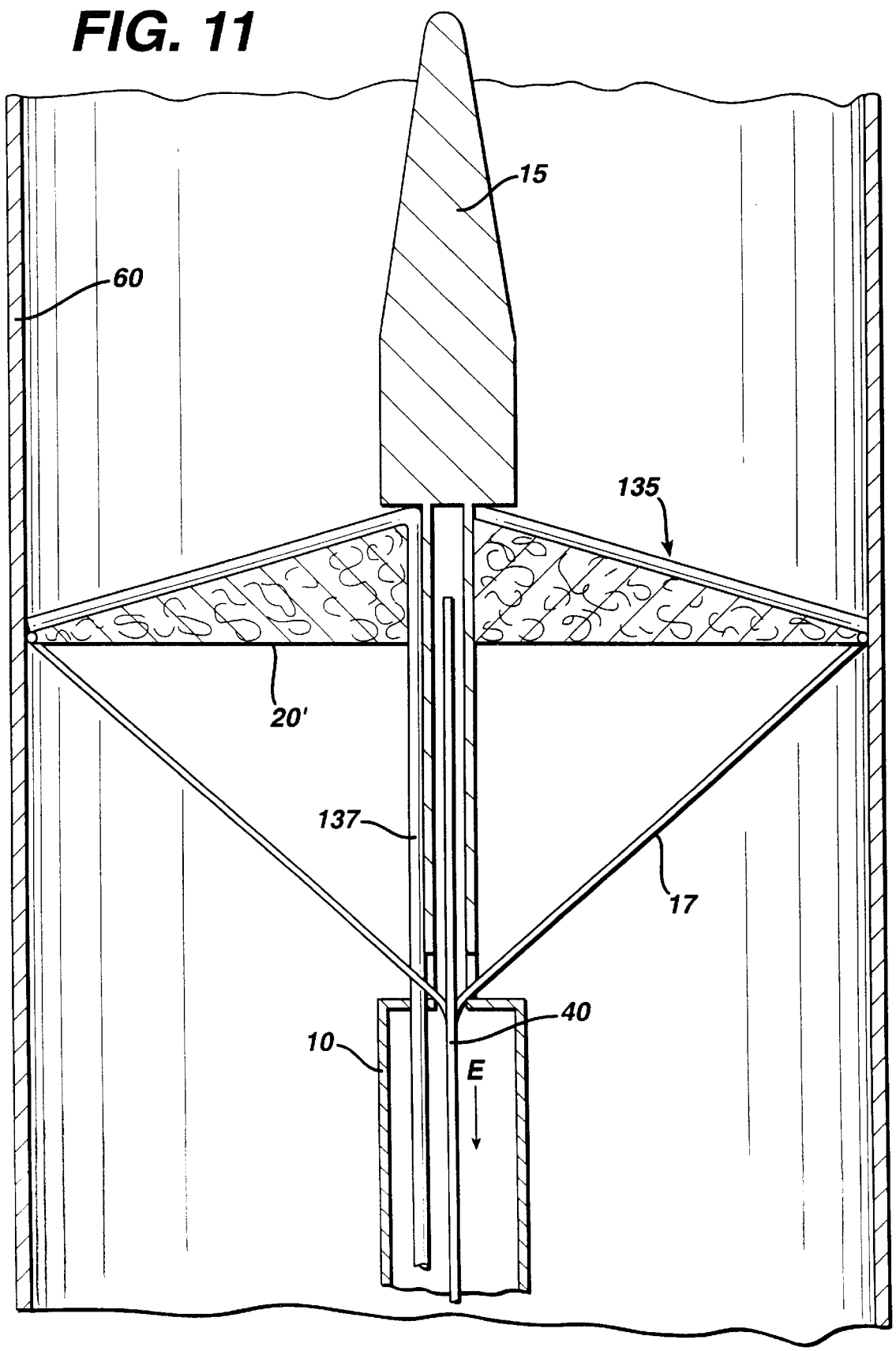
FIG. 11 is a partial cross-sectional view of another embodiment of the invention having inflatable support spines.

In yet another embodiment of the invention shown in FIG. 11, filter membrane 20 can be supported by inflatable spines 135 supporting the filter membrane 20. Spines 135 supporting the filter membrane 20 are from two to six hollow plastic tubes which are inflatable using, for example, a standard balloon angioplasty inflation device or endoflator in fluid connection through channel 137 with spines 135. Inflation of spines 135 causes them to become rigid and deploys filter membrane 20. The underside of the filter membrane is attached to very thin fibers 17 which are attached to moveable core 40 inside hollow guidewire 10. Filter membrane 20 is collapsed by deflating the spines 135 and withdrawing the moveable core 40 in the direction of arrow E until the membrane 20 fits tightly against guidewire 10.

Figure 7:
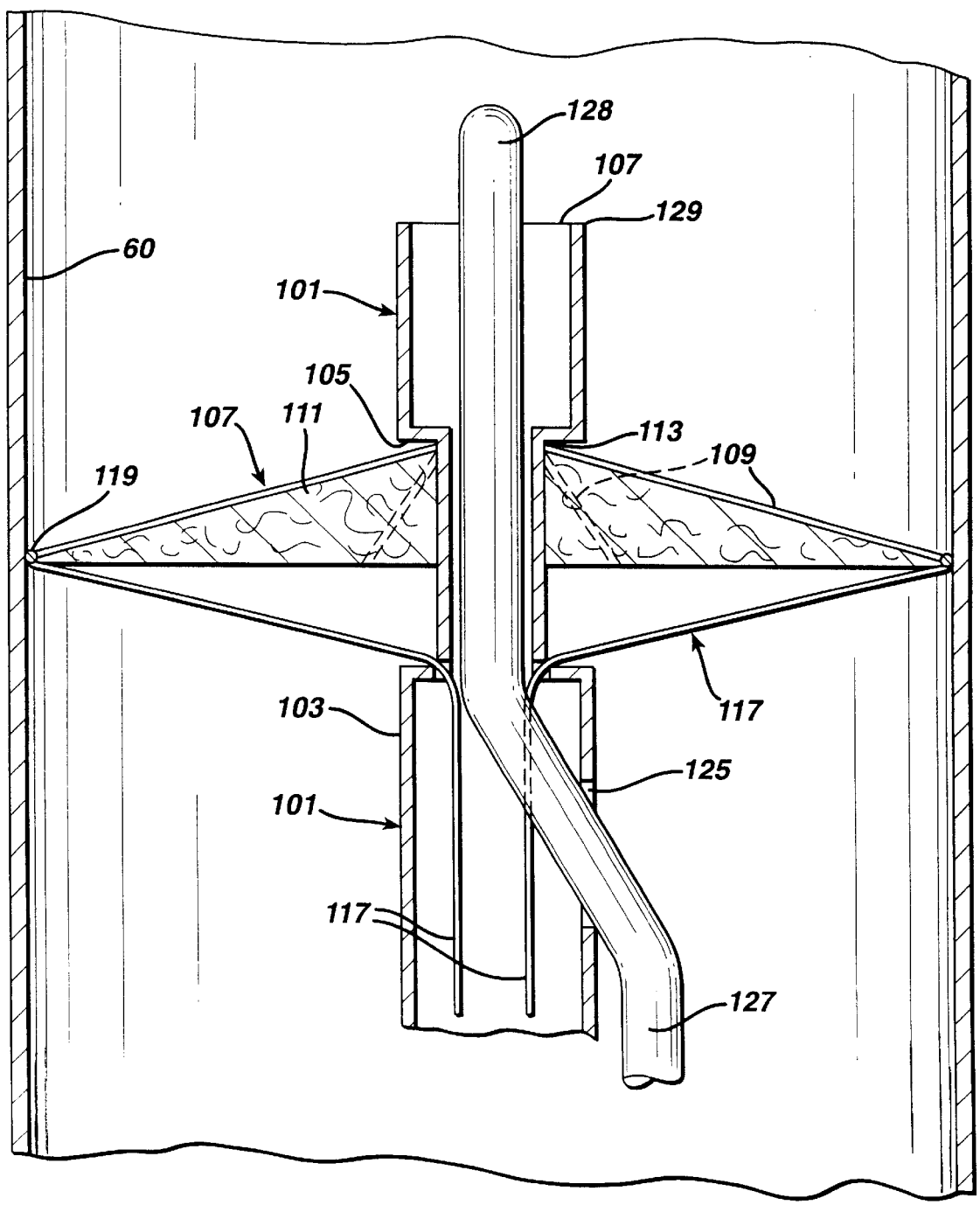
FIG. 7 is a partial cross-sectional view of another embodiment of the invention.

A catheter-based configuration is also possible, as shown in FIG. 7. In this design the guidewire and filter catheter are two separate components. The filter catheter has an entry hole for the guidewire and the guidewire exits out the end of the filter catheter. The filter catheter could be designed to accommodate a variety of guidewire sizes, most commonly a 0.014 inch guidewire. The advantages of this design are that a variety of guidewires may be used; the lesion is crossed with the guidewire prior to crossing with the filter catheter; the filter catheter is removed from the artery without removing the guidewire; and the filter catheter is made smaller.

In the embodiment of the invention shown in FIG. 7, a catheter 101 comprises a longitudinally extending lumen 103, which as an annular recess 105 adjacent the distal end of catheter 101. Positioned within recess 105 is a filter 107 comprised of structural wires 109 and a filter membrane 111. The distal end of each, of wires 109 is attached at point 113 in recess 105. Fibers 117 extend from the proximal ends 119 of wires 109 proximally to a control means such as described in FIG. 6.

Catheter 101 contains guidewire port 125 located proximal to recess 105. It is intended that in use the distal portion 128 of a guidewire 127 will be threaded into the distal end 129 of catheter 101 and out through port 125.

Alternately, (not shown here) a catheter 101 could comprise a longitudinally extending lumen and a shorter tracking lumen that extends from distal end 129 to a point proximal to recess 105. The distal end of guidewire 127 would then be threaded into the distal opening of the tracking lumen and out the proximal end of the tracking lumen.

Figure 8:
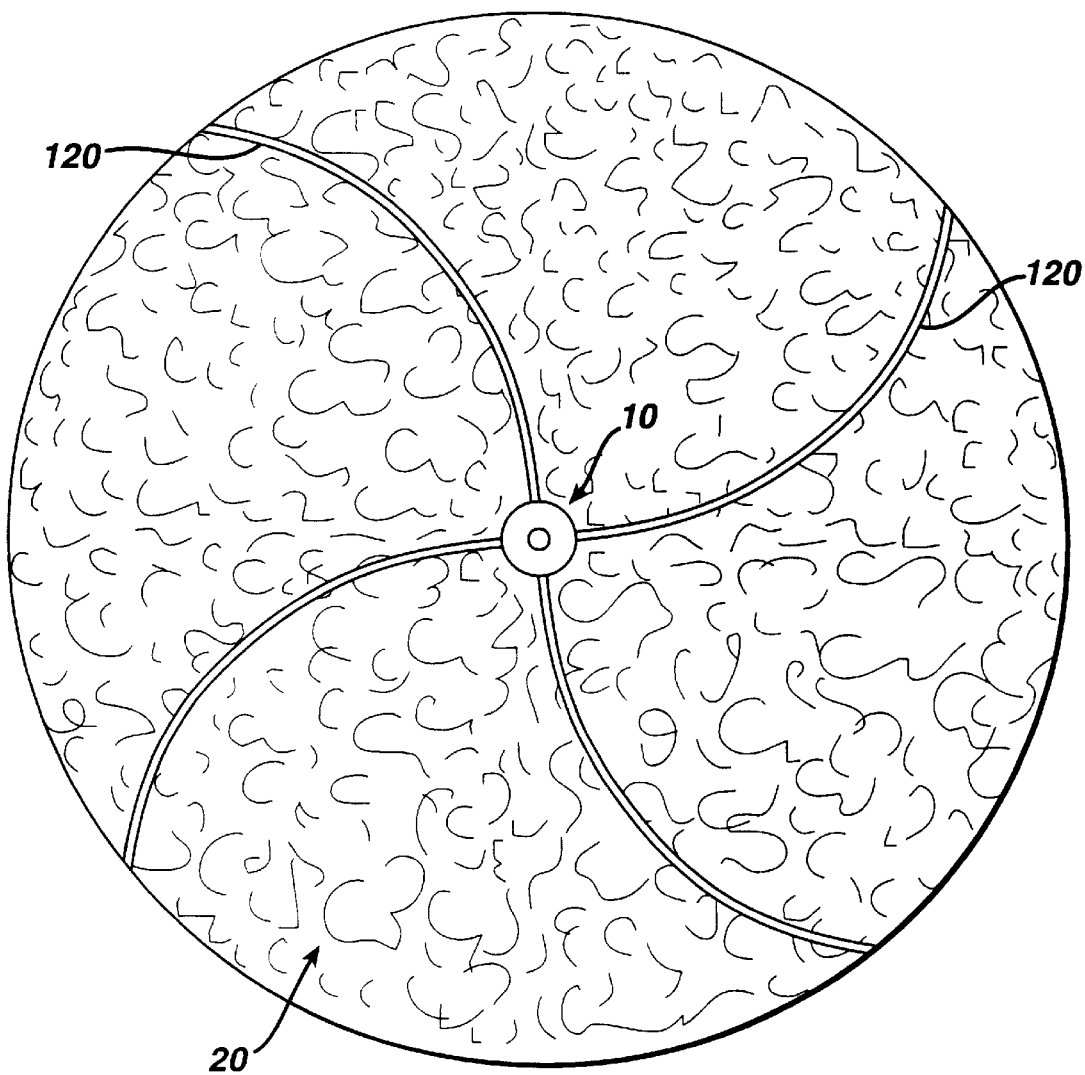
FIG. 8 is a partial cross-sectional view of an embodiment of the invention in which the filter membrane has curved supports.

Spiral or curved structural wires may be used to deploy the filter membrane instead of straight wires. FIG. 8 illustrates the use of four curved wires 120. The angulation of the filter attachment point of wires 120 relative to their guidewire attachment has the effect of wrapping the filter fabric around the guidewire in the undeployed state. This leads to a lower profile for the undeployed filter.

Figure 9:
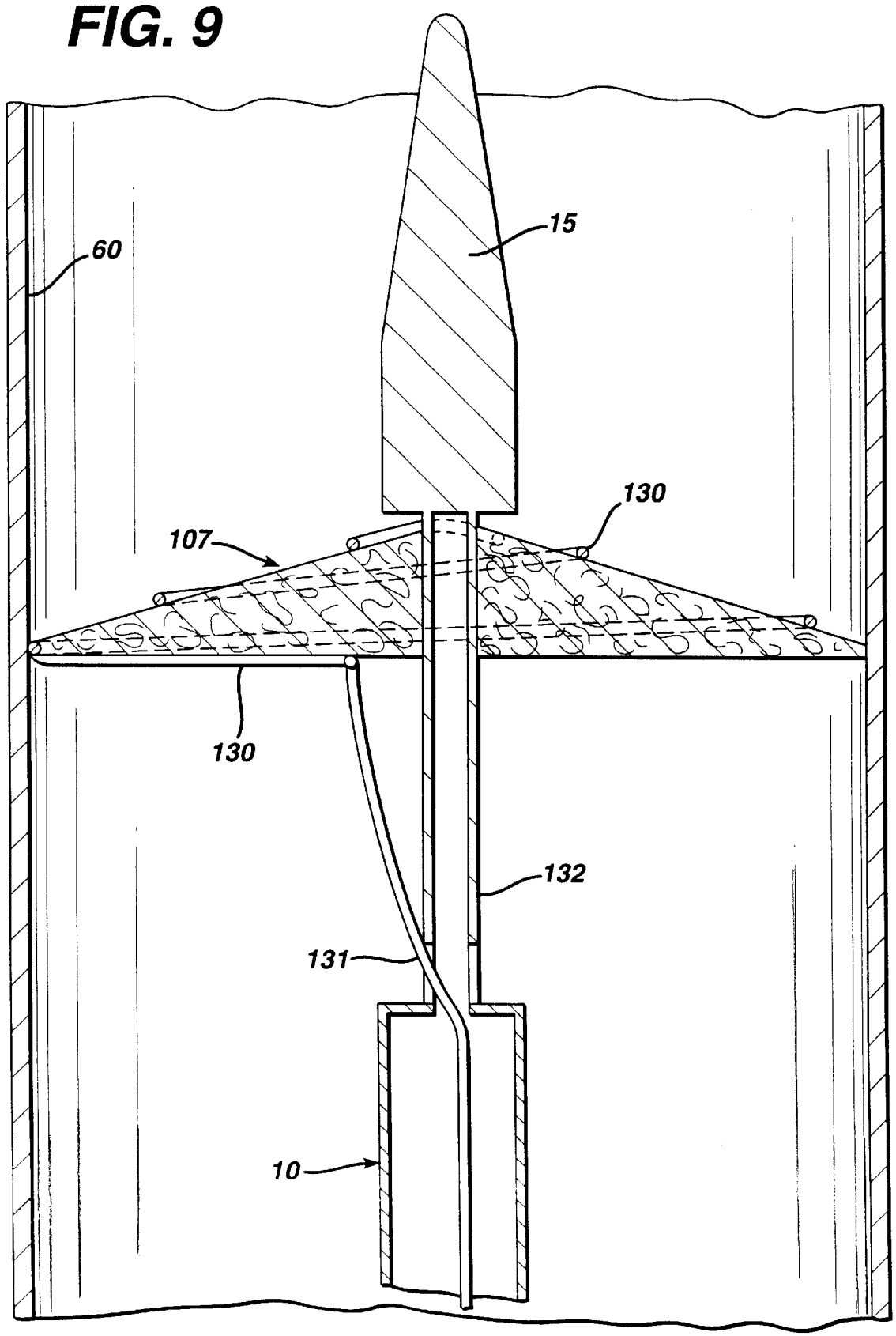
FIG. 9 is a partial cross-sectional view of yet another embodiment of the invention in which the filter membrane has a spiral wire.
Figure 10:
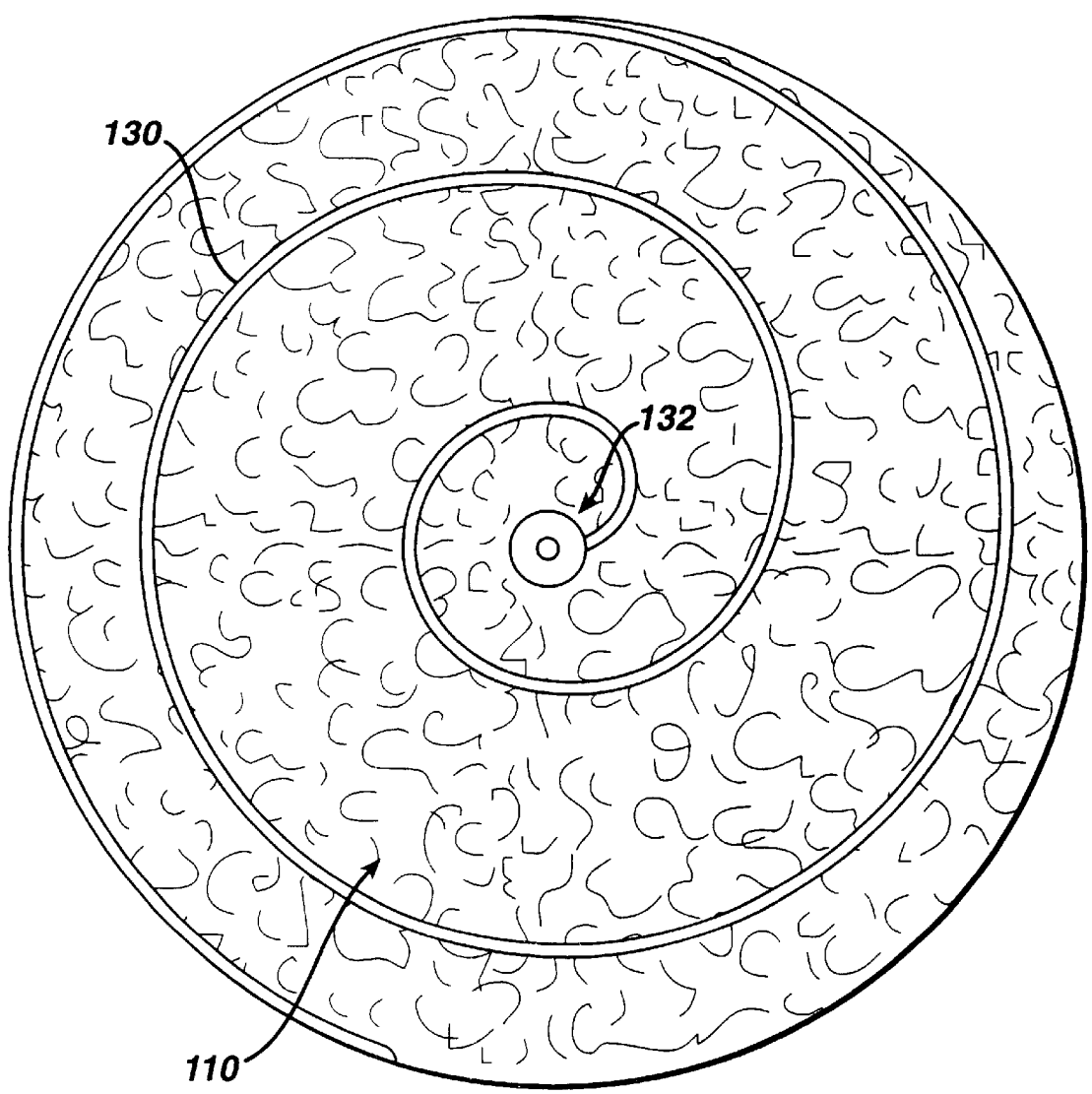
FIG. 10 is a top cross-sectional view of the embodiment of the invention shown in FIG. 9.

FIGS. 9 and 10 illustrate the use of a single spiral structural wire 130 which is attached to the filter 107. As tension fiber 131 is released, wire 130 unwinds and deploys filter 107 in a conical configuration. This configuration has the simplicity of using a single wire and, when the tension on fiber 131 is increased, allows filter 107 to be wrapped very tightly around the guidewire shaft 131, resulting in filter 107 having a low profile in its undeployed state.

Figure 12:
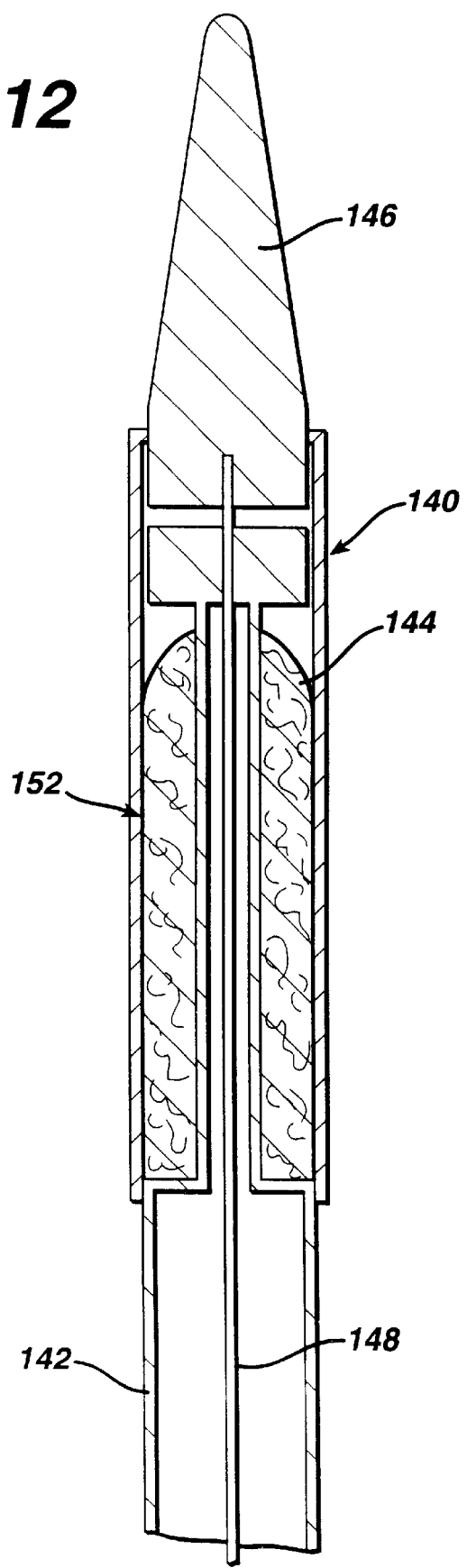
FIGS. 12 and 13 represent partial cross-sectional views of another embodiment of the invention in collapsed and deployed positions, respectively.
Figure 13:
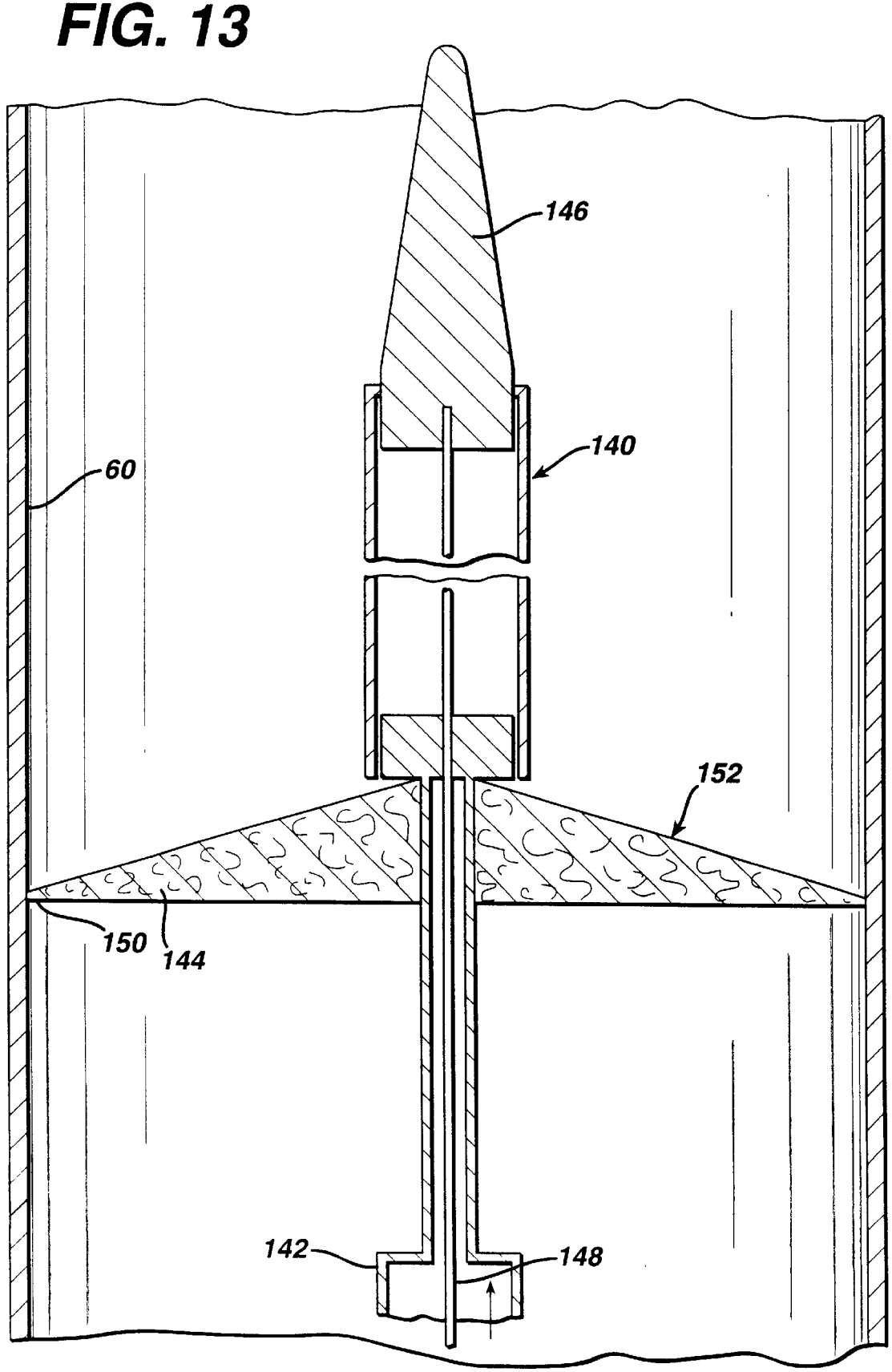

Another modification shown in FIGS. 12 and 13 comprises a retractable sheath 140 at the distal end of guidewire 142 which covers filter membrane 144 in the collapsed state. The distal portion of sheath 140 is affixed to guidewire tip 146; tip 146 is affixed to the distal end of moveable core 148. This prevents an edge 150 of filter membrane 144 from becoming entangled in an artery or guide catheter during withdrawal from a patient.

More specifically, when guidewire 142 with tapered tip 146 is inserted percutaneously into a patient, sheath 140 covers collapsed filter membrane 144. After the filter membrane is determined (usually by fluoroscopy) to be in proper position, moveable core 148 is pushed distally to cause sheath 140 to "release" from filter membrane 144, which has spines 152. This causes filter membrane 144 to deploy, as shown in FIG. 13.

FIG. 14 illustrates a lateral, cross-sectional view of a distal end of a guidewire 160 with a filter membrane 170 attached thereto. FIG. 14 shows guidewire 160 with a shapeable soft (sometimes referred to as "floppy") tip 162 at its extreme distal end, to provide flexibility and maneuverability to guidewire 160. The filter membrane in FIG. 14 is in an open position.

Guidewire 160 comprises a core wire 164, which extends into floppy tip 162, and sheath 166. Filter membrane 170 is supported by a basket 169 comprising two or more filter basket wires 168, having distal ends 172 and proximal end 174. The distal ends 172 of basket wires 168 are fixedly attached to core wire 164 by distal radiopaque marker or crimp band 176, and the proximal ends 174 of basket wires 168 are attached to proximal radiopaque marker or crimp band 178, which is slidable over core wire 164, optionally with a polymeric (such as polyimide) or metallic sleeve between core wire 164 and proximal ends 174. Optionally, and preferably, proximal marker 178 is fixedly attached to core wire 164, and distal marker 176, with a polymeric or metallic sleeve, is slidable over core wire 164.

A sheath member 180 is attached to the distal end of sheath 166, sheath member 180 having a lumen 182 with a diameter and length sufficient to receive or slide over proximal marker 178. Sheath 166 and sheath member 180 can be either separate bonded pieces or a continuous, integral structure. Sheath 166 and sheath member 180 are each made from low friction polymeric material, preferably polytetrafluoroethylene, polyethylene, nylon, or polyurethane.

Filter membrane 170 can comprise a number of different metallic or nonmetallic permeable membranes having sufficient porosity to facilitate blood flow, but having sufficiently small openings to capture emboli. Filter membrane 170 must be affixed at least at its distal portion 184 to core wire 164 and/or basket wire distal ends 172 and, optionally, to basket wires 168. The remainder of filter membrane 170 can be unattached or, preferably, attached to basket wires 168, such as by a suitable adhesive. Preferably basket wires 168 are encapsulated in membrane 170.

Basket 169 can be somewhat cylindrical in its middle with conically tapered proximal and distal portions. Alternatively, basket 169 can be slightly spherical, optionally with a cylindrical flat middle portion. Preferably basket 169 is from about 5 to about 40 mm in length and from about 2 to about 30 mm, or from about 2 to about 20 mm in diameter, at its widest.

The proximal end of sheath 180 is attached to control handle or guidewire torquer 186. Control handle 186 has an opening 188, for core wire 164 so that sheath 180 can move slidably over core wire 164. For example, when sheath 180 is moved distally toward basket wires 168, filter membrane 170 collapses. Also, there may be instances where sheath 180 will be removed proximally so that other catheters or cardiovascular appliances can be introduced over core wire 164. Control handle 186, which functions as a torque device, also primarily functions to lock sheath 180 to core wire 164 during insertion.

There are a number of known, commercially available guidewire torquers that may be modified to function as control handle 186. Modification includes, but is not limited to, providing a slightly larger central lumen.

In FIG. 15 sheath 166 and sheath member 180 are shown advanced distally so that basket wires 168 and filter member 170 are collapsed against core wire 164. The distal end 192 of sheath member 180 may optionally be slightly tapered to provide a better profile for insertion.

Figure 16:
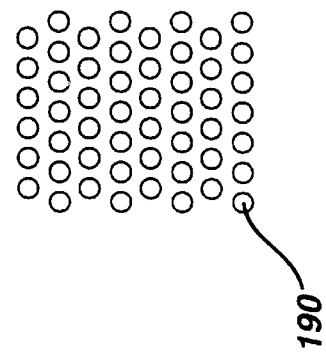
FIG. 16 is a schematic representation of a portion of a filter membrane according to the invention.

In a preferred embodiment of the invention, as shown in FIG. 16, filter membrane 170 comprises a polymeric material such as polyurethane or silicone elastomer that has laser-drilled holes 190. Such holes 190, a pattern for which can be seen in FIG. 16, are preferably only on the conical portion of filter membrane 170. The holes 190 could be from about 50 to 300 $\mu$m in diameter. The vertical separation of holes 190 can be from 1.2 to 1.4 times the hole diameter and the center-to-center diameter of holes 190 can be from about 1.4 to 1.6 times the hole diameter. In a preferred embodiment, the vertical and horizontal spacing of the holes is such that the center-to-center spacing of the holes is from about 1.2 to 2.0 times the hole diameter. Preferably, the open area of the holes represents from about 10 to 50 percent, more preferably from about 15% to 40%, of the filter surface.

Basket wires 168 are made of a suitable, physiologically acceptable material. Stainless steel or nitinol are preferred, although titanium or other metal alloys could be used.

Figure 17:
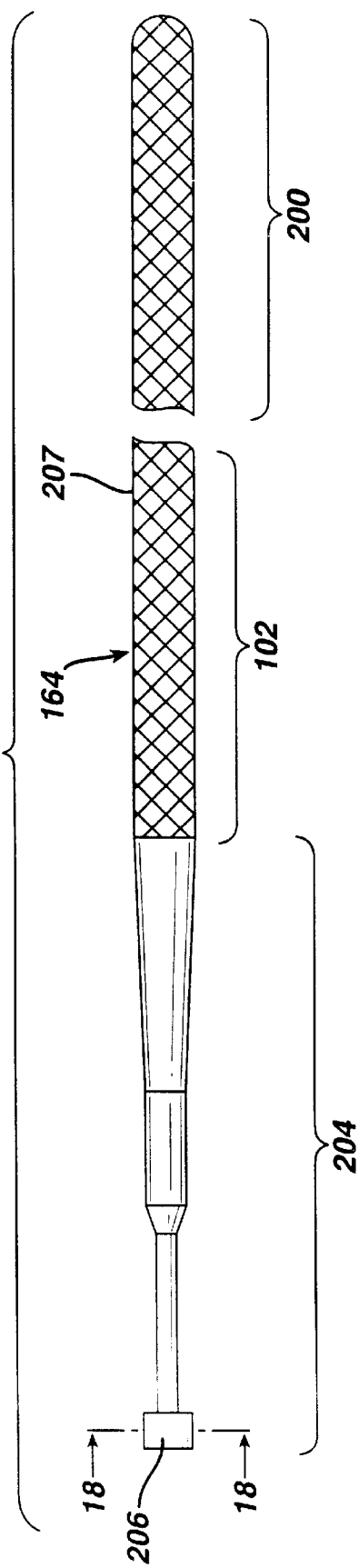
FIG. 17 is a lateral view of a core wire useful according to the invention.
Figure 18:
FIG. 18 is a cross-sectional view across line 18—18 of a portion of the core wire of FIG. 17.

Core wire 164 can be seen better in FIG. 17, where the proximal and middle portions 200 and 202 are substantially uniform in diameter, and then the distal portion 204 tapers to an end point 206. In fact, distal portion 204 could taper uniformly or, more preferably, non-uniformly, as shown in FIG. 17. Typically, core wire 164 is from about 250 to 300 cm in length, with an initial diameter of from about 0.009 in. to 0.038 in., preferably from about 0.014 in. to 0.018 in. Distal section 204 is typically from about 8 to 10 cm in. total, with a diameter that tapers to from about 0.001 in. to 0.005 in. Core wire 164 may optionally have a thin polymeric coating 207 for friction reduction. Preferably end point 206 is a solid, squat cylinder, as shown in FIGS. 17 and 18.

Floppy tip 162 preferably comprises a radiopaque helical spring 210 that is fixedly attached, e.g., by welding, brazing, or soldering, to end point 206 and, optionally, attachment point 208. Optionally spring coil 210 may have a polymeric or lubricious coating 212.

Figure 19:
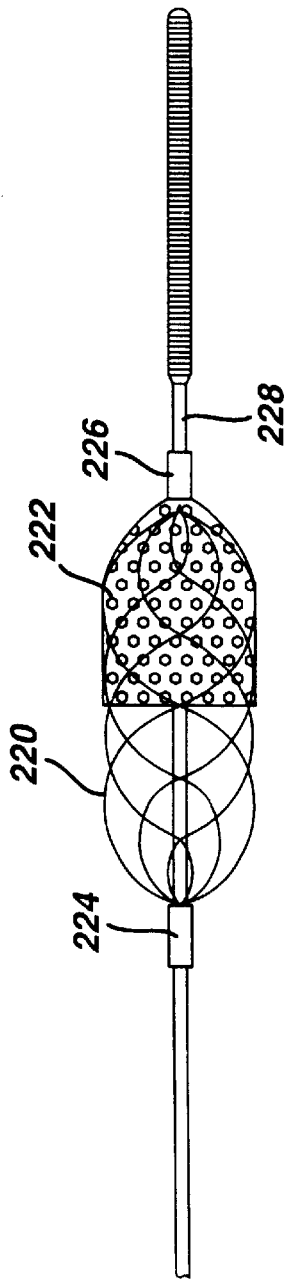
FIG. 19 is a lateral, cross-sectional view of an alternative basket structure for the embodiment of FIG. 14.

FIG. 19 represents yet another alternate design. Basket wires 220 are substantially helical in shape. Filter member 222 covers or encompasses the distal portion of basket wires 220. Proximal and distal portions of basket wires 220 are secured by proximal radiopaque marker or crimp band 224 and distal radiopaque marker or crimp band 226, respectively. Markers 224 and 226 are fixed or slidable on core wire 228 as described above. Preferably there are from 4 to 8 basket wires 220, each with a rotation of from about 45° to 360°.

Figure 20:
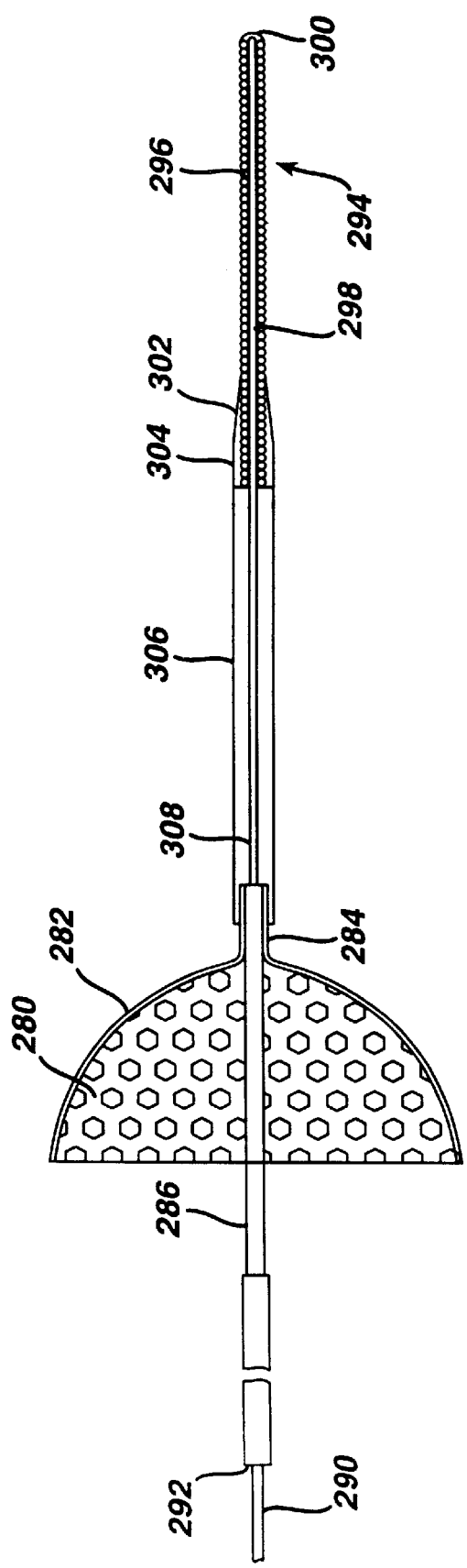
FIG. 20 is a lateral, partial cross-sectional view of another embodiment of the invention.
Figure 21:
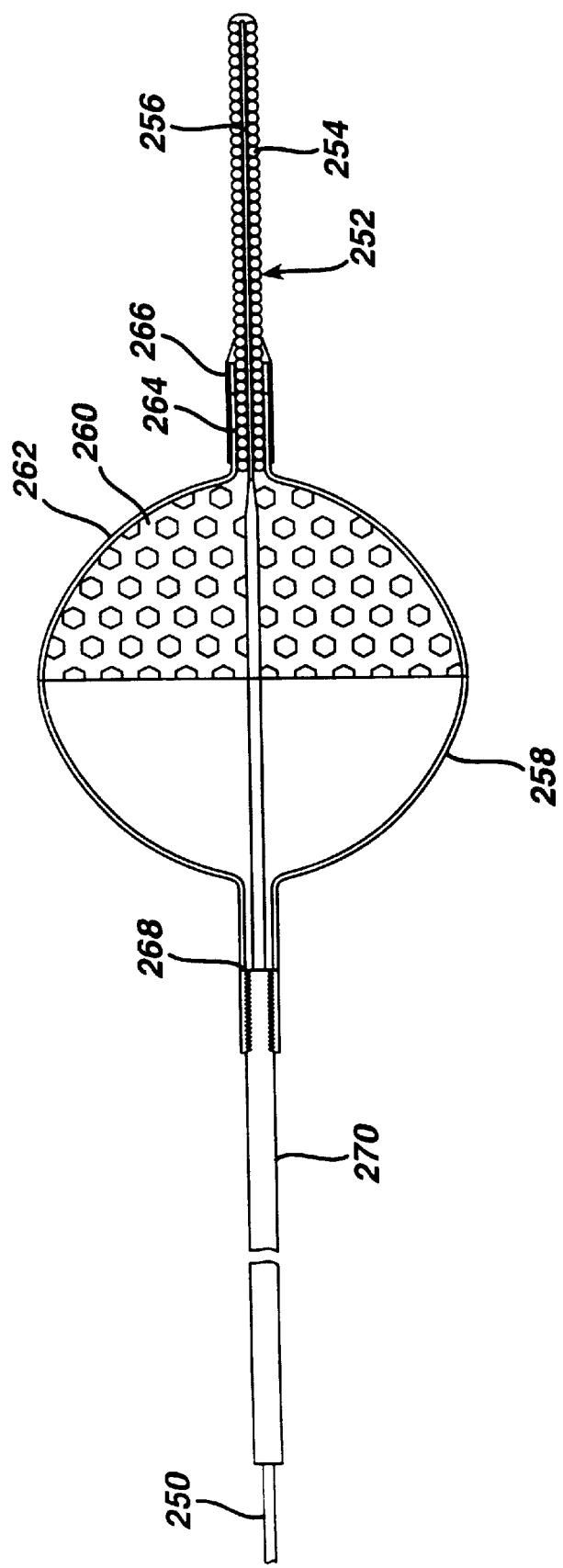
FIG. 21 is a lateral, partial cross-sectional view of a further embodiment of the invention.

Additional embodiments of the invention can be seen in FIGS. 20 and 21. The schematic representation in FIG. 20 depicts a filter membrane 280 supported by strut wires 282. The distal ends 284 of strut wires 282 are attached to the distal portion of a tubular member 286. A movable core wire 290 extends through a lumen 292 in tubular member 286 to distal floppy section sections 294, where a helical spring coil 296 surrounds the distal portion 298 of core wire 290 and is attached to end point 300. An attachment point 302 of weld or solder at the proximal portion of spring coil 296 where the distal portion 304 of sheath member 306 is also attached to core wire 290. The lumen 308 of sheath member 306 is large enough so that as core wire 290 is pulled proximally, or tubular member 286 is advanced distally, the distal ends 284 of strut wires 282 move into lumen 308 and collapse filter membrane 280.

Moveable core wire 250 of the structure shown in FIG. 21 comprises a floppy tip 252 where a helical spring coil 254 encompasses the distal portion 256 of core wire 250. A basket wire structure component of two or more basket wires 258 supports a filter membrane 260 on the distal portion 262 of the basket structure. Distal ends 264 of the basket wires 258 are encompassed by a radiopaque market or crimp band 266 that is attached to core wire 250 and/or spring coil 254. The proximal ends 268 of basket wires 258 are attached to the distal portion of a sheath 270 that surrounds core wire 250. Sheath 270 moves slidably over core wire 250 so that when sheath 270 is pulled proximally into core wire 250, filter membrane 260 collapses.

In FIG. 22 a basket 320 comprised of from 4 to 8 strut wires 322 is secured by a distal fixed grommet 324 and a proximal slidable grommet 326. Grommet 326 is slidable over core wire 328. Filter membrane 330 is attached to or arranged upon basket 320, with the proximal section 332 of the membrane 390 being open to flow, represented by arrows 334. The distal portion 336 of membrane 330 forms a conical shape 340 that extends proximally. The filter could be deployed by, for example, a sheath or a tube fixed to the proximal slidable crimp band 336. This design is optimized for perfusion and emboli collection. For example, as more emboli is collected, it tends to collect in non-filter areas, leaving the pores open for perfusion.

Membrane 330 preferably has holes only in the distal section 336/340, which holes are arranged as described above. It is believed that under normal, (substantially laminar) flow conditions debris or emboli 342 will tend to collect in annular recesses 344.

To close and capture emboli, as shown in FIG. 23, slidable grommet 326 is moved proximally to collapse basket 320 and membrane 336. This can be accomplished with, for example, sheath 350 or a fixed tubular member or other apparatus that is preferably slidable over the core wire.

Figure 24:
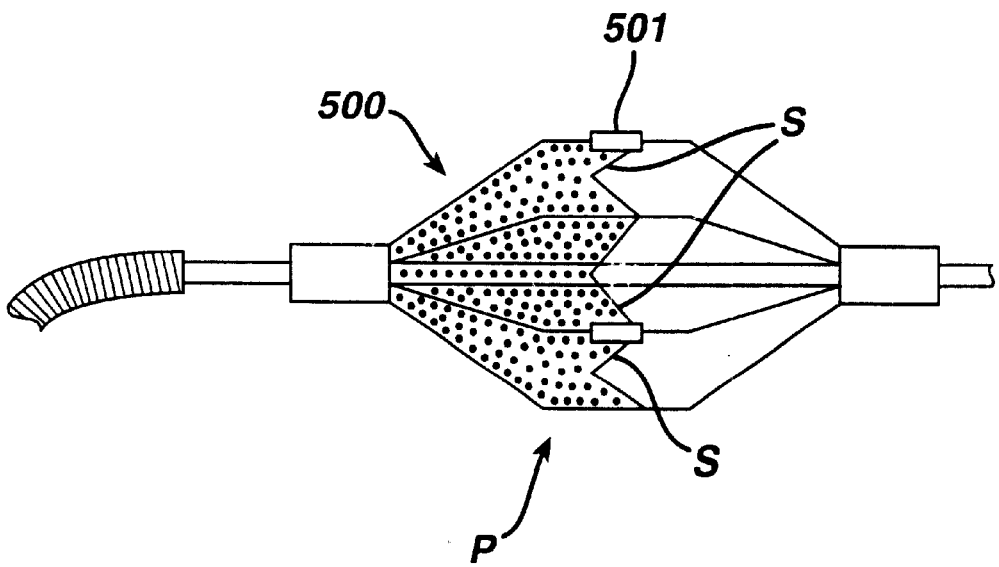
FIGS. 24, 25, 26 and 27 are schematic views of other modifications of the present invention.
Figure 25:
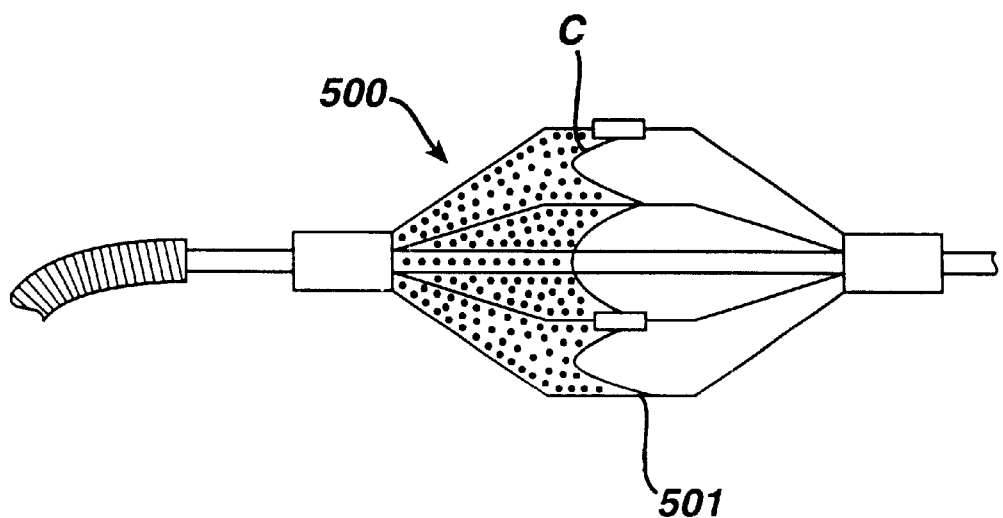

Various modifications of the current invention are described in the appended FIGS. 24 through 27. As seen in FIGS. 24 and 25, a slight modification of the profile p of the filter membrane 500 will result in easier folding of the membrane inwardly either prior to or subsequent to capture of embolic material. That is, as seen in FIG. 24, the membrane is provided with a scallops S forming profile P. As seen in FIG. 25, the profile P contains more curves C, shaped somewhat like a bat's wings. The scallop shapes "S", as seen in FIGS. 24 and 25 are intended to be shapes in which the unfurled profile of the filter membrane is such that there are alternate longer and shorter sections around the circumference of the stent in the shape of a scallop. In either event however, this reduced leading edge profile for the filter membrane 500 allows for easier folding of the membrane subsequent to its collection of embolic material. The membrane 500 folds more readily because at its distal ends 501 folds, there is less material to be placed in-close juxtaposition. Accordingly, this type of fold will enable the material to be captured, and yet also provide for more ready disposition of the membrane.

The membrane 500 can be cut in such a profile by standard techniques, including among other things, laser cutting, as is discussed above.

Figure 26:
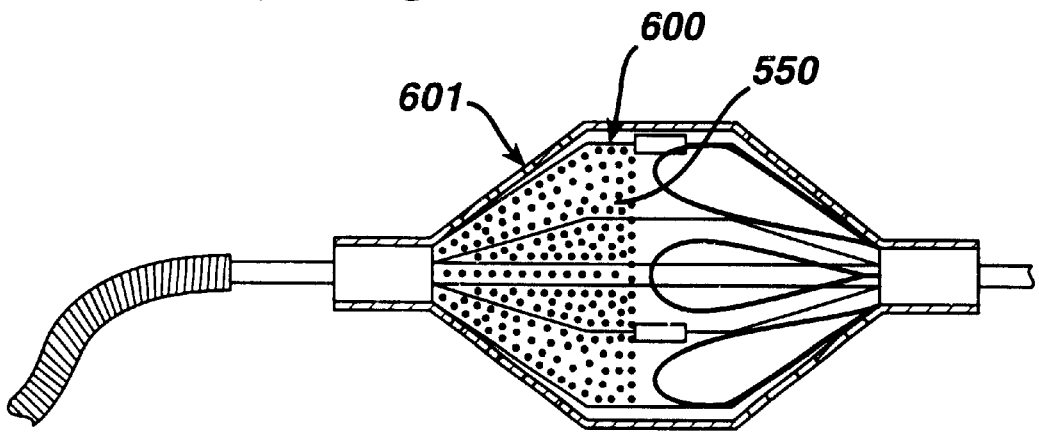

As seen in the embodiment of FIG. 26, a balloon 601 is incorporated outside the basket element 600 of the filter membrane 550 so that element 600 "floats" inside the balloon 600. In this embodiment, the balloon 601 is placed outside of the filter mechanism 550. The balloon 601 is then laser drilled, creating larger holes for entrance of embolic articles. A basket is thus formed "inside" the balloon. The balloon is then seated as a basket only at its distal end. In this fashion, the filter element is incorporated into the profile of a balloon and so is further able to provide for embolic capture.

Figure 27:
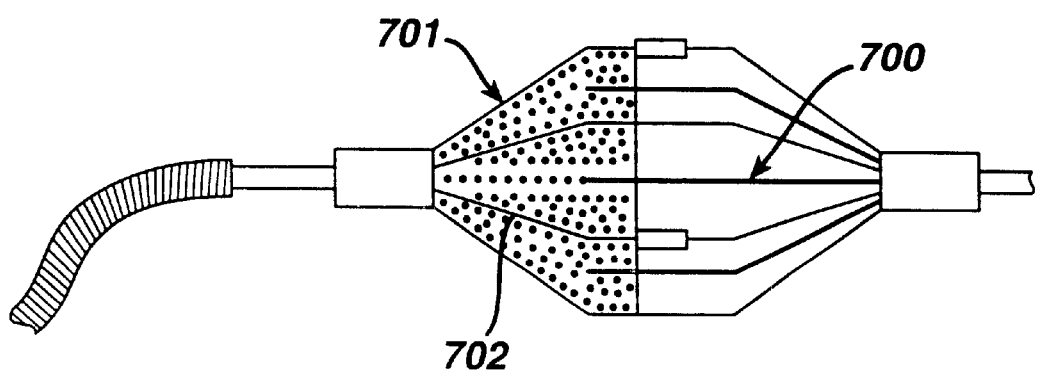

As seen in FIG. 27, struts 700 are placed intermediate the struts 702 used to fold the membrane 701 inward during collapse. These struts provide for greater stability of the membrane 701 during emplacement in the artery. For even further stability, there could be placed smaller struts (not shown) bridging these fingers.

It is to be understood that any of the embodiments described herein can be made by laser cutting the membrane mechanism possibly even into a self expanding hypo tube. Further, the mechanism can be made by dipping the device into a bath containing the polymer of the membrane. In this fashion, the dimensional depth of the bath can be adjusted to provide for optimal performance of the membrane material.

The wires, membrane, and other materials of this embodiment are consistent with those described above.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A removable vascular filter system comprising:
   a guidewire having distal and proximal ends,
   a filter membrane having a distal portion and a proximal free end portion, wherein said distal portion is pivotably attached to the guidewire near said distal end of the guidewire and wherein the proximal free end portion is substantially parallel to the guidewire in its collapsed state and wherein said free end portion has a generally scalloped shape; and deploying means for causing the filter membrane to assume a position substantially normal to the longitudinal axis of the guidewire.

2. The vascular filter system of claim 1, whereby the deploying means comprises a control mechanism at the proximal end of the guidewire operatively connected to the filter.

3. The vascular filter system of claim 1, wherein the filter membrane is comprised of a porous mesh, and the scalloped shape is comprised of straight or rounded sections.

4. The vascular filter system of claim 3, wherein the pore size of the porous mesh is from about 20 to about 300 microns.

5. A removable vascular filter system comprising:

a guidewire having distal and proximal portions and defined by a longitudinal axis, wherein there is a recess in the distal portion, the recess having distal and proximal ends, a filter membrane having an inner portion and a free end portion, wherein the inner portion is attached to the guidewire near the distal end of the guidewire recess and wherein the free end portion is positioned in the recess when the filter membrane is in a collapsed state, and wherein the filter membrane in an unstressed position assumes a position substantially normal to the longitudinal axis of the guidewire;

means for collapsing the filter membrane from a deployed state to a collapsed state; and a network of struts comprising a deploying mechanism, said struts having alternating longer and shorter lengths and arranged circumferentially about said longitudinal axis.

* * * * *